(12) United States Patent
Sakal et al.

(10) Patent No.: US 7,674,434 B2
(45) Date of Patent: Mar. 9, 2010

(54) VIALS AND APPARATUS FOR OBTAINING AN ALIQUOT OF A SAMPLE

(75) Inventors: Robert Sakal, Bolton, MA (US); Hal Watts, Holden, MA (US); Steve Scampini, Groton, MA (US)

(73) Assignee: Cytyc Corporation, Marlborough, MA (US)

( * ) Notice: Subject to any disclaimer, the term of this patent is extended or adjusted under 35 U.S.C. 154(b) by 448 days.

(21) Appl. No.: 11/563,639

(22) Filed: Nov. 27, 2006

(65) Prior Publication Data

US 2008/0121050 A1 May 29, 2008

(51) Int. Cl.
 *B01L 3/00* (2006.01)
(52) U.S. Cl. .................. 422/102; 422/100; 422/101
(58) Field of Classification Search ............. 436/180; 422/100–102
 See application file for complete search history.

(56) References Cited

U.S. PATENT DOCUMENTS 6,866,820 B1 3/2005 Otto et al.

| 2002/0001542 | A1 | 1/2002 | Itoh |
| 2003/0059347 | A1 | 3/2003 | Ostgaard |

FOREIGN PATENT DOCUMENTS

| EP | 0344819 | 12/1989 |
| JP | 06324052 | 11/1994 |
| JP | 2004157020 | 6/2004 |
| WO | 03031275 | 4/2003 |
| WO | 2005014173 | 2/2005 |

OTHER PUBLICATIONS

PCT Invitation to Pay Additional Fees and Communication Relating to the Results of the Partial International Search, Forms PCT/ISA/206 and Annex to Form PCT/ISA/206, for PCT/US2007/085146, Applicant Cytyc Corporation, dated Mar. 26, 2008 (6 pages).
PCT International Search Report for PCT/US2007/085146, Applicant CYTYC Corp., Forms PCT/ISA/210 and 220, dated Jun. 10, 2008 (9 pages).
PCT Written Opinion of the International Search Authority for PCT/US2007/085146, Applicant CYTYC Corp., Form PCT/ISA/237, dated Jun. 10, 2008 (11 pages).

*Primary Examiner*—Yelena G Gakh
*Assistant Examiner*—David Weisz
(74) *Attorney, Agent, or Firm*—Vista IP Law Group LLP

(57) ABSTRACT

Vials used for obtaining an aliquot of a biological sample are provided. Also provided are method of using the vials and instruments to obtain an aliquot of a biological sample.

11 Claims, 8 Drawing Sheets

VIALS AND APPARATUS FOR OBTAINING AN ALIQUOT OF A SAMPLE

FIELD OF THE INVENTION

The invention pertains to the preparation of cytological samples, and more specifically, to a method and apparatus for obtaining aliquots from cytological samples, such as fluid-based Papanicolaou ("Pap") smears.

BACKGROUND

When a liquid-based Pap smear is performed, a biological specimen sample (cellular material) is obtained from the patient, from which a specimen slide is prepared. The specimen slide is then evaluated, e.g., by a cytotechnologist, and typically classified by the cytotechnologist as either "normal" or "abnormal." An abnormal sample normally falls in one of the major categories defined by The Bethesda System for Reporting Cervical/Vaginal Cytologic Diagnosis, which categories include Low-Grade Squamous Intraepithelial Lesions (LSIL), High-Grade Squamous Intraepithelial Lesions (HSIL), Squamous Cell Carcinoma, Adenocarcinoma, Atypical Glandular cells of Undetermined Significance (AGUS), Adenocarcinoma in situ (AIS), and Atypical Squamous Cell (ASC), which can be further sub-divided into Atypical Squamous Cell, cannot exclude HSIL (ASC-H) and Atypical Squamous Cell of Undetermined Significance (ASC-US).

A specific Human Papilloma Virus (HPV) deoxynucleic acid (DNA) test, referred to as the Hybrid Capture II HPV DNA assay, manufactured by Digene Corporation, has been used to determine whether patients, whose Pap smears have been classified as ASC-US, have HPV. Based on the strong correlation between HPV and cervical cancer, it has been recommended that HPV DNA testing be used as a triage test for patients whose Pap smear results are classified as ASC-US.

In the case where a liquid-based Pap smear has been performed, the same sample used to perform the Pap smear analysis can be conveniently used to perform a "reflexive" HPV DNA test, thereby obviating the need for a repeat clinic visit and second Pap smear. In this case, if a slide is positive for ASC-US, an aliquot (e.g., 4 mL) of the fluid sample is removed from the stored vial and sent to a molecular diagnostic laboratory for HPV DNA testing.

Significantly, laboratories that perform HPV DNA tests are weary of molecular contamination—a well-known problem in molecular diagnostic laboratories. Thus, due to the risk of cross-contamination, molecular diagnostic laboratories may not accept aliquots that have been taken from an already processed liquid-based Pap smear for fear of unnecessarily generating false HPV positives.

SUMMARY OF THE INVENTION

In one embodiment, a biological sample container comprises a vial, configured for holding the biological sample; and a vial cap configured to removably seal the vial, wherein an access port is disposed on the vial cap and adapted to admit a needle therethrough to obtain an aliquot of the biological sample. The access port can be self-sealing, for example by a rubber septum. Alternatively, the access port may be sealed by a removable cover or cap. In some embodiments, the vial cap further comprises a chamber adapted to hold a volume of liquid. The chamber can comprise a sealable opening facing the interior of the vial. The chamber may further comprise a flexible membrane coplanar with the top surface of the vial cap, the flexible membrane configured to cause the sealable opening to open when the flexible membrane is depressed.

In another embodiment, a biological sample container comprises a first chamber, a second chamber, a dispensing tip, wherein the first chamber is in fluid communication with the second chamber through a first passageway, and the second chamber is in fluid communication with the dispensing tip through a second passageway. A first one way valve is provided along the first passageway and configured to allow at least a portion of the biological sample to flow from the first chamber to the second chamber, but not flow in reverse. A second one way valve is provided along the second passageway and configured to allow the portion the biological sample to flow out from the second chamber to the dispensing tip, but not flow in reverse. A plunger is provided to draw the biological sample from the first chamber to the second chamber through the first passageway when the plunger is moved in a first direction, and to draw the biological sample from the second chamber to the dispensing tip through the second passageway when the plunger is moved in a second direction. By way of non-limiting example, the plunger can comprise a flexible squeeze bulb. Alternatively, the plunger may comprise a piston. The dispensing tip can be adapted to fit a receiving tip of a sample tube, where the dispensing tip can further comprise a removable cap.

In still another embodiment, a biological sample container comprises first chamber in fluid communication with a second chamber via a passageway. A one way valve is provided along the passageway and configured to allow at least a portion of the biological sample to flow from the first chamber to the second chamber, but not flow in reverse. A flow control valve is also provided along the passageway, wherein, when the flow control valve is in an open position, fluid communication between the first and second chambers is established. A plunger is provided to draw the biological sample from the first chamber to the second chamber through the passageway. The second chamber may be removable. In some embodiments, the plunger is in gaseous communication with the second chamber.

In another aspect, the presently disclosed inventions include a method of obtaining an aliquot of a biological sample disposed in a container, the container comprising a vial containing the biological sample, a vial cap, and an access port disposed on the vial cap. In one embodiment, the method comprises placing the container inside an automated processor; automatically inserting a syringe through the access port into the vial; transferring an aliquot of the biological sample into the syringe; automatically removing the syringe from the vial; dispensing the transferred aliquot of the biological sample from the syringe into a sample tube; and placing the container and the sample tube in an output tray. The method may further comprise uncapping the access port prior to inserting the syringe, as well as capping the access port after removing the syringe. The method may also optionally comprise capping the sample tube after dispensing the transferred aliquot. In optional embodiments, the aliquot of the biological sample is transferred into the syringe using vacuum. The method can further comprise placing the container in a first output tray and placing the sample tube in a second output tray.

In another embodiment, the method comprises obtaining an aliquot of a biological sample disposed in a container, the container comprising a first chamber containing the biological sample, a second chamber in fluid communication with the first chamber, and a plunger, the method comprising transferring the container from a storage location to a location within an automated processor using a first mechanical arm; moving the plunger with a second mechanical arm in a first direction, thereby causing a portion of the biological sample to flow from the first chamber into the second chamber; and placing the container in an output tray. The method may further comprise agitating the sample prior to moving the plunger. By way of non-limiting examples, the plunger may comprise a flexible squeeze bulb, or a piston. In some embodiments, the second mechanical arm comprises a grasper to grasp a handle on the plunger.

In some embodiments, the container may further comprise a dispensing tip in fluid communication with the second chamber, and the method may further comprise connecting a sample tube to the dispensing tip with a third mechanical arm; moving the plunger with the second mechanical arm in a second direction, thereby causing the portion of the biological sample to flow from the second chamber into the sample tube through the dispensing tip; disconnecting the sample tube from the dispensing tip; and placing the sample tube in an output tray. The method can further comprise uncapping the sample tube and/or the dispensing tip prior to connecting the sample tube to the dispensing tip. In some embodiments, the container and the sample tube are placed in the same output tray, whereas in other embodiments, the container is placed in a first output tray and the sample tube is placed in a second output tray. In some embodiments, the container can further comprise a flow control valve, and therefore the method further comprises opening the flow control valve with an actuator prior to moving the plunger. The second chamber can be removable.

In still another aspect, embodiments of the invention include an instrument for obtaining an aliquot of a biological sample, comprising a first mechanical arm configured for retrieving and positioning a vial adjacent to a syringe, the vial having a cap and the cap having an access port, the syringe configured for being inserted through the access port to the interior of the vial; and a vacuum source in gaseous communication with the syringe. The instrument can further comprise an agitator configured for mixing the contents of the vial. The agitator can mix the contents of the collection chamber by one or more of rotating the vial, shaking the vial, and applying ultrasound energy to the contents of the collection chamber. The first mechanical arm can be further configured to retrieve the vial from a storage location and deliver it to the agitator. Additionally, the first mechanical arm can be further configured deliver the vial to an output tray. In further embodiments, the instrument can further comprise a second mechanical arm configured to retrieve a sample tube and deliver it to the syringe. The second mechanical arm can also be further configured to deliver the sample tube to an output tray.

In yet another aspect, embodiments of the invention include an instrument for obtaining an aliquot of a biological sample stored in a vial, the vial having a first chamber, a second chamber, and a plunger, the instrument comprising a first mechanical arm configured for retrieving the vial from a first storage location; and a second mechanical arm configured to move the plunger in a first direction. The instrument can further comprise an agitator that receives the vial from the first mechanical arm, the agitator configured for mixing the contents of the vial, where the agitator can mix the contents of the collection chamber by one or more of rotating the vial, shaking the vial, and applying ultrasound energy to the contents of the collection chamber. The first mechanical arm can be further configured to place the vial in an output tray. In the embodiments where the vial can further comprise a dispensing tip, the instrument can further comprise a third mechanical arm configured to retrieve a sample tube and deliver it to the dispensing tip of the vial. The second mechanical arm can be further configured to move the plunger in a second direction. The third mechanical arm can be further configured to deliver the sample tube to an output tray.

BRIEF DESCRIPTION OF THE DRAWINGS

It will be appreciated that the drawings are not necessarily to scale, with emphasis instead being placed on illustrating the various aspects and features of embodiments of the invention, in which.

Figure 1:
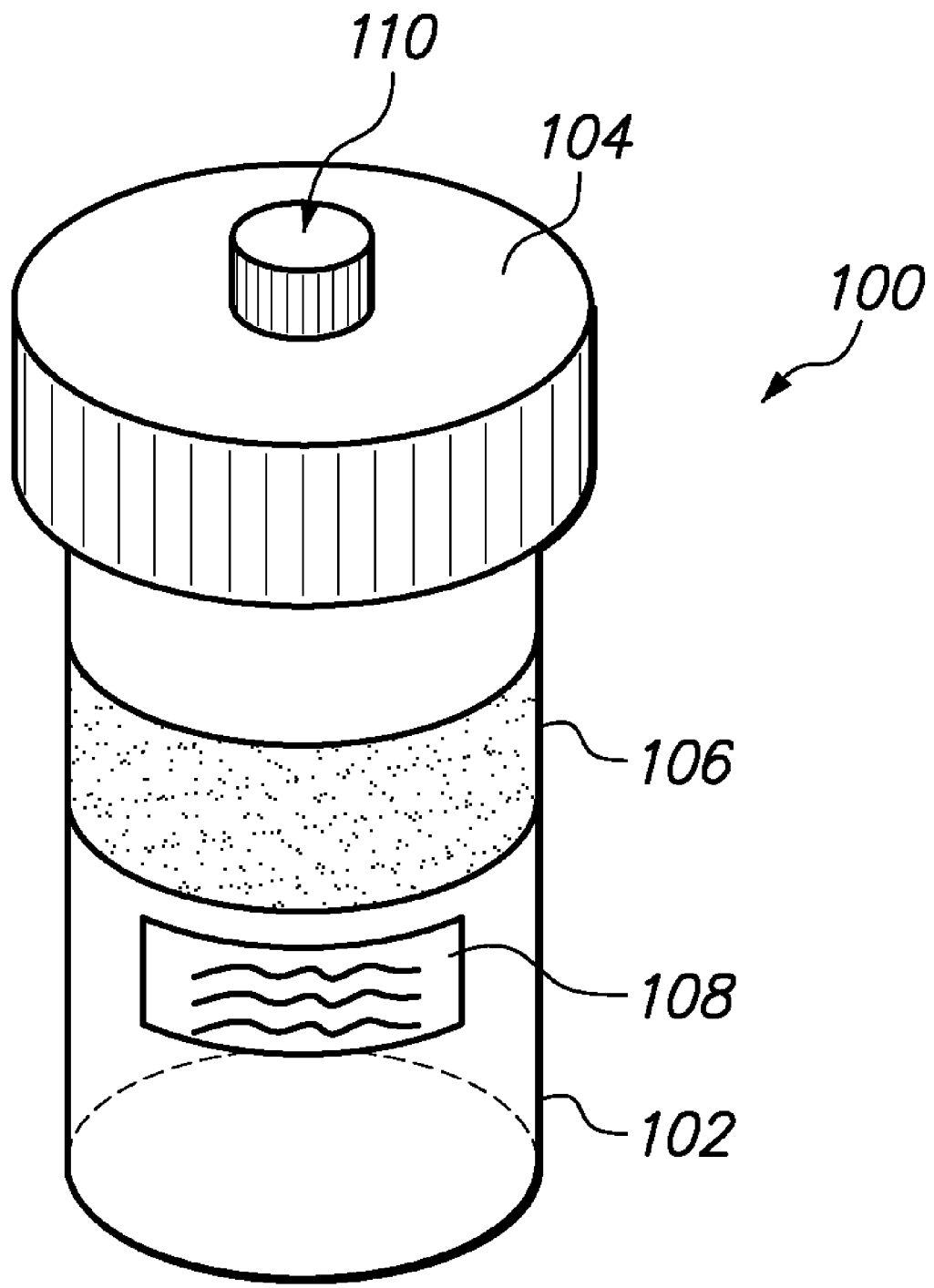
FIG. 1 is an illustration of an embodiment of a sample vial comprising an access port in its cap.

DETAILED DESCRIPTION OF THE
ILLUSTRATED EMBODIMENTS

Referring to FIG. 1A, a sample vial 100 constructed in accordance with one embodiment of the present invention will be described. The vial 100 may be used to contain a fluid-based sample, such as a cervical-vaginal sample collected from a patient at a physician's office. The fluid-based sample typically comprises cytological material suspended in an aqueous preservative fluid.

To this end, the vial 100 comprises a hollow vial container 102 and a vial cap 104 that can be placed onto the vial container 102 to enclose a sample contained within the vial container 102. As depicted, the vial container 102 and vial cap 104 are generally cylindrical in shape. The selected size of the vial container 102 and vial cap 104 may vary, but preferably is large enough to contain the minimum amount of sample necessary to perform the intended diagnostic test. In the illustrated embodiment, the vial container 102 is capable of containing at least 20 mL of fluid, which is the minimum amount of sample required by the Food and Drug Administration (FDA) for automated transfer onto a microscope slide using Cytyc's ThinPrep® 2000 or Thinprep® 3000 slide preparation systems. For example, the vial container 102 may have an outer diameter of approximately 1 and 5/16 inches and an axial length of approximately 2 and 3/4 inches, and the vial cap 104 may have an outer diameter of approximately 1 and 9/16 inches and an axial length approximately 7/16 of an inch.

The vial container 102 is composed of a translucent or transparent material to allow a user to determine the fluid level inside of the vial 100. A suitable material is a plastic, such as polypropylene homopolymer, available under the trade designation AMOCO 4018. The vial cap 104 may be releasably mated with the vial container 102 using a standard threaded engagement (not shown), and may be composed of a plastic material, such as polypropylene random copolymer, available under the trade designation AMOCO 8949. The materials of which the vial container 102 and vial cap 104 are composed may be injection molded to rapidly and inexpensively produce the container 102 and cap 104, although other suitable manufacturing processes may be utilized depending on the particular materials selected.

A seal (not shown) may be disposed between the vial container 102 and cap 104 to form a fluid-tight seal when sufficient torque is applied to the cap 104 relative to the container 102. Sealing is important to prevent both leakage and evaporation of the preservative solution in the vial container 102, as well as to prevent the sample from being exposed to external contaminants. The seal may be composed of any material or materials capable of withstanding attack by the preservation solution in the vial container 102, which typically includes an alcohol solution, such as methanol in a buffer. Due to the low viscosity and high vapor pressure of the preservative solution, as well as the very low density and high permeability of the vapor phase thereof, a high integrity, reliable, seal composition is desired. Further, because the vial 100 may be stored for a year or more prior to use, and be subject to temperature extremes during transport and storage, the seal should be capable of retaining its sealing characteristics and structural integrity for extended periods of time without excessive loss of fluid due to evaporation. The seal material also should not degrade and contaminate the sample. In one embodiment that meets these requirements, the seal is composed of a multicomposite material, including a sufficiently thick, dense, resilient layer disposed on a vapor barrier. The resilient layer may be oriented toward the sample to provide an effective seal. The seal may include a synthetic olefin rubber or an elastomeric alloy co-extruded on a thin vapor barrier, such as that available from Tri-Seal, Inc., located in Blauvelt, N.Y., and sold under the trade name TRI SEAL SOR-117.

The vial container 102 includes a fluid level indicia 106 by which a user may determine a proper amount of preservation fluid to fill the vial 100 or that the vial 100 is filled properly prior to addition of the cytological material. The fluid level indicia 106 may be a frosted annular band of a predetermined axial length disposed about a circumference of the vial container 102 at a predetermined axial location to indicate the acceptable fill range of the vial 100, so that a proper slide sample can be prepared from the sample by an automated specimen preparation system, such as Cytyc's ThinPrep® 2000 or ThinPrep® 3000 slide preparation systems. Alternatively, the fluid level indicia 106 may be a single fill line or an upper fill line and a lower fill line, in which case, the upper fill line indicates a maximum level to which the vial container 102 should be filled and the lower fill line indicates a minimum amount of fluid necessary to prepare a specimen from the sample.

The vial container 102 also includes sample indicia 108, which can be used to identify a patient to whom the sample corresponds, as well as a slide prepared from the sample contained in the sample vial 100. The sample indicia 108 may be machine-readable, such as a bar code, which can be ready by an automated cytological specimen preparation system, such as Cytyc's ThinPrep® 2000 or ThinPrep® 3000 slide preparation systems.

In an optional embodiment, the vial container 102 and vial cap 104 may be specially configured for automated manipulation. For example, the vial container 102 may have laterally protruding anti-rotation lugs (not shown), and the vial cap 104 may have a torque pattern of ribs (not shown), thereby allowing the cap 104 to be screwed on and screwed off of the vial container 102 using automated machinery. Additional details regarding these features are disclosed in U.S. patent application Ser. No. 09/156,952, entitled "Sample Vial for Use in Preparing Cytological Specimen," which is fully and expressly incorporated herein by reference.

Figure 2A:
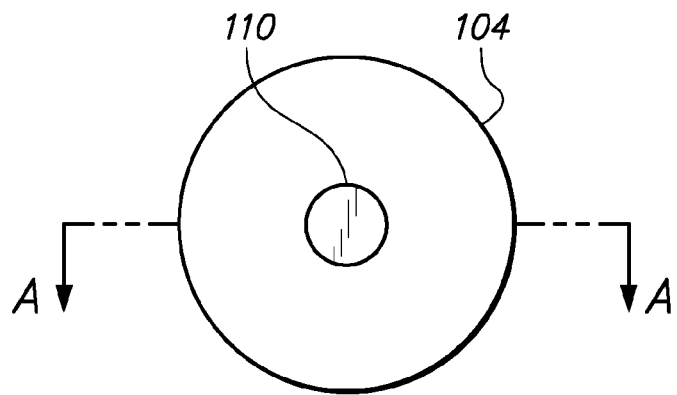
FIG. 2A is a top view of an embodiment of the cap of the vial of the embodiment shown in FIG. 1, where the access port is centered.

The vial cap 104 comprises a sealed access port 110 to allow access, for example by a syringe or a pipette, to the sample within the vial container 102 without the need to unscrew the cap 104. FIG. 2A illustrates an embodiment in which the access port 110 is centered on the vial cap 104.

Figure 2B:
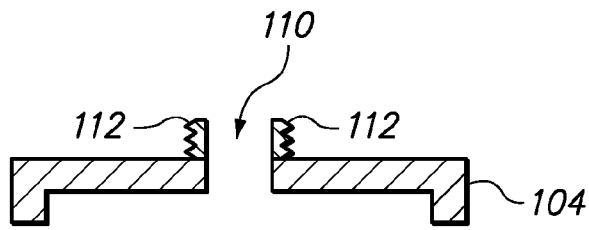
FIG. 2B is a cross sectional view of the embodiment of vial cap of FIG. 2A cut along the A-A line, showing the access port.
Figure 2C:
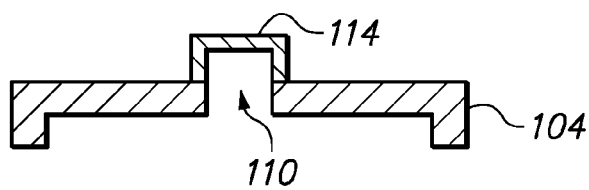
FIG. 2C is another cross sectional view of the embodiment of vial cap of FIG. 2A cut along the A-A line, where the access port is capped.

FIG. 2B is a cross-sectional view of one embodiment of the cap 104 of FIG. 2A cut across the A-A line. A threaded arrangement 112 is provided around the access port 110 on the upper side, or outside, of the vial cap 104. A port cap 114, as shown in FIG. 2C, is provided to seal the access port 110 by being twisted over the access port 110 and the threaded arrangement 112. Thus, the inside of the vial container 102 can be accessed by twisting the port cap 114 off, obtain access through the access port 110, and then re-seal the access port 110 by twisting the port cap 114 back on again. Preferably, a seal, such as the seal described above between the vial cap 104 and the vial container 102, is also provided between the port cap 114 and the threaded arrangement 112 to prevent leakage, evaporation of the sample, or contamination of the sample by outside contaminants. In an optional embodiment, the port cap 114 may be specially configured for automated manipulation. For example, the port cap 114 may have a torque pattern of ribs (not shown), thereby allowing the port cap 114 to be screwed on and screwed off of the vial cap 104 using automated machinery.

Figure 2D:
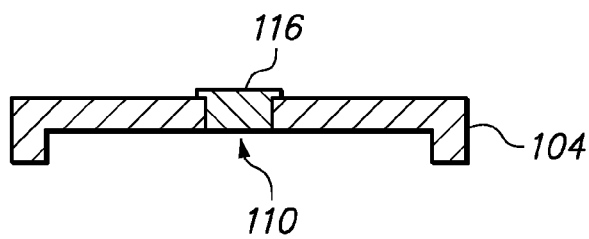
FIG. 2D is another cross sectional view of the embodiment of vial cap of FIG. 2A cut along the A-A line, where the access port is sealed with a septum.

FIG. 2D is a cross-sectional view of another embodiment of the cap 104 of FIG. 2A cut across the A-A line. In this embodiment, the access port 110 comprises a sealing mechanism in the form of septum 116 seated within the access port 110 to seal it, thereby preventing fluid, or air, communication between the inside and the outside of the vial container 102 until a user is ready to remove an aliquot sample from the vial container 102 for examination. User access to the vial container 102 can be accomplished, e.g., by puncturing the septum 116 with a syringe (not shown) and drawing the aliquot sample from the vial container 102 into the syringe.

Figure 2E:
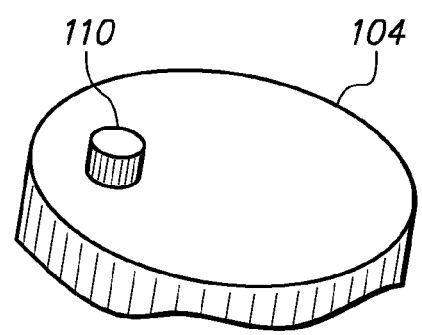
FIG. 2E is an illustration of another embodiment of the cap of the vial of the embodiment shown in FIG. 1, where the access port is off centered.

In some embodiments, such as the one shown in FIG. 2E, the access port 110 is off-centered. The access port 110 in these embodiments can be capped, analogous to the embodiment shown in FIG. 2C, or sealed by a septum, analogous to the embodiment shown in FIG. 2D.

Often, when an aliquot of sample is removed from the vial container 102, more solution needs to be added to the vial container 102 to bring the volume of the sample within the vial 102 back to the original level. For example, usually the vial container 102 contains 20 mL of solution containing a biological sample. An aliquot of 4 mL is removed from the vial container 102 for further examination. Before a sample slide from the biological sample within the vial container 102 can be prepared, 4 mL of a solution, such as PreservCyt®, would have to be added to the vial container 102 to bring the volume of the sample within the vial container 102 back to 20 mL, in order to comply with the FDA requirements for the operation of Cytyc's ThinPrep® 2000 or ThinPrep® 3000 slide preparation systems.

In some embodiments, the user can add 4 mL of the preservative solution to the vial by introducing the solution through the access port 110, for example, by injecting the solution using a syringe. However, introducing new solution to an already existing biological sample can cause outside contaminants to be introduced into the sample.

Thus, in another aspect, disclosed herein is a vial comprising a vial cap, where the vial cap comprises an access port and a solution chamber.

Figure 3A:
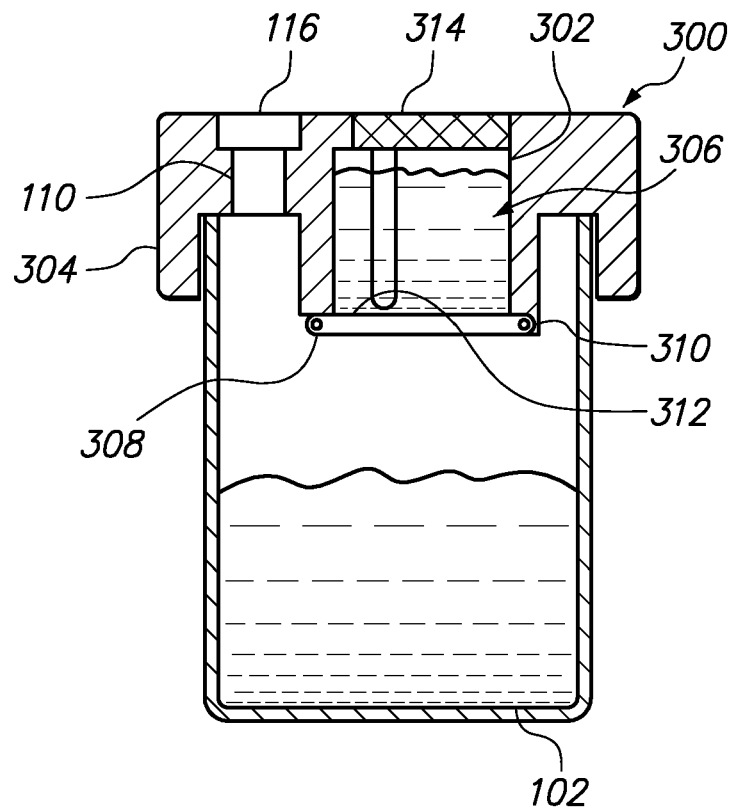
FIG. 3A is an illustration of another embodiment of a sample vial comprising a solution chamber in its cap, where the solution chamber is closed.
Figure 3B:
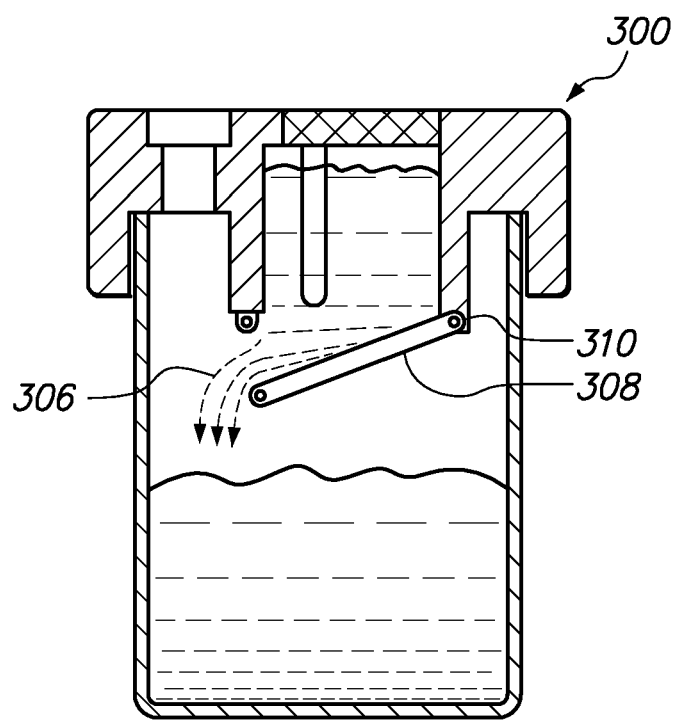
FIG. 3B is an illustration of the embodiment of sample vial of FIG. 3A, where the solution chamber is open.

FIGS. 3A and 3B illustrate an embodiment of the vial 300, which comprises a vial cap 304. The vial cap 304 comprises an access port 110 sealed with a septum 116. Alternatively, the access port 110 can be sealed with a cap, as discussed above. The vial cap 304 further comprises a solution chamber 302 constructed within the vial cap 304. The solution chamber 302 is configured to hold a volume, e.g., 4 mL, of a solution 306. The solution 306 can be water, alcohol, or a buffered solution. Preferably, the solution 306 is Preserv-Cyt®, marketed by Cytyc Corp. (www.cytyc.com).

The solution chamber 302 is sealed at the bottom by a hinged flap 308, as shown in FIG. 3A, which can pivot about a hinge 310. The flap 308 is held in the closed position using a locking mechanism 312. The locking mechanism 312 can be a friction lock or a nub and groove lock. The locking mechanism 312 is strong enough to hold the flap 308 in the closed position during the normal use and transportation of the vial container 102 and prevent accidental opening. However, the lock mechanism 312 is also responsive enough to allow the flap 308 to open when the user so intends (see below). When the flap 308 is in the closed position it prevents any fluid communication between the solution chamber 302 and the inside of the vial container 102.

A flexible membrane 312 defines the top perimeter of the solution chamber 302. When the flexible membrane 312 is depressed, for example by the user or by an automated instrument (discussed below), it creates positive pressure within the solution chamber 302. The positive pressure within the solution chamber 302 is of sufficient force to cause the locking mechanism 312 to unlock. The flap 308 then pivots about the hinge 310 and rests in an open position, as shown in FIG. 3B. Consequently, the solution 306 flows from the solution chamber 302 into the inside of the vial container 102.

The use of vial 100 allows the user to obtain and store an aliquot prior to the preparation of a slide sample by, for example, ThinPrep® 2000 or ThinPrep® 3000. This imparts the advantage significantly minimizing the likelihood of contamination of the aliquot due to the ThinPrep process.

Figure 4A:
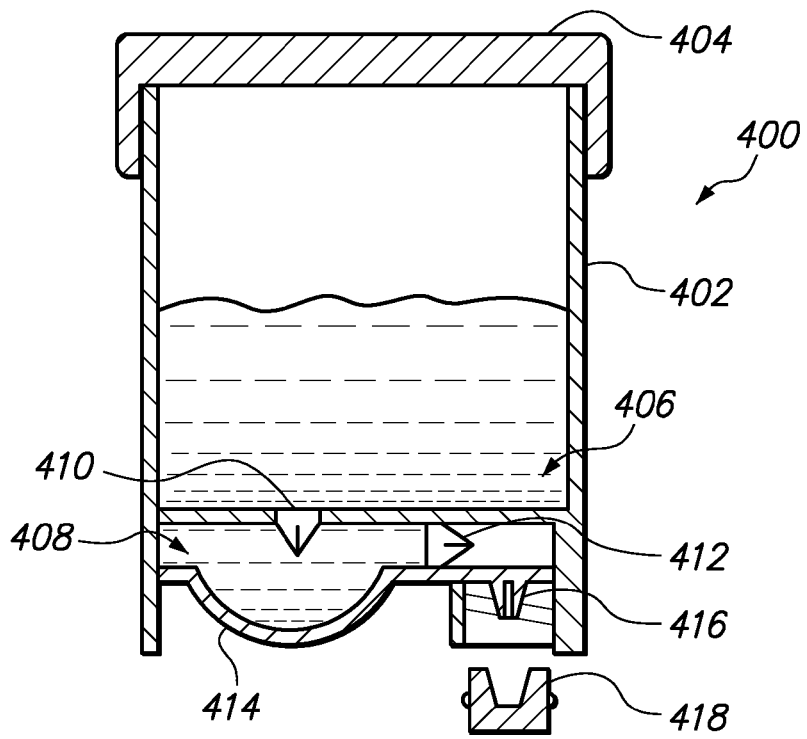
FIG. 4A is an illustration of another embodiment of a sample vial comprising an aliquot chamber at the bottom of the vial, where the aliquot chamber comprises a squeeze bulb mechanism.

Referring to FIG. 4A, a vial 400 constructed in accordance with another embodiment comprises a vial cap 404, includes a feature that allows an aliquot sample to be taken and isolated from the sample contained within the vial container 402. In particular, the vial 400 comprises a collection chamber 406 formed within the vial container 402 for collection of the sample and an aliquot chamber 408 for containing the aliquot sample. A one-way valve mechanism 410 connects the aliquot chamber 408 to the collection chamber 406. Fluid can flow from the collection chamber 406 to the aliquot chamber 408 through the valve 410, but fluid cannot flow in the reverse direction, i.e., from the aliquot chamber 408 to the collection chamber 406. An aliquot, for example 4 mL of the sample within the collection chamber 406, can thus be transferred from the collection chamber 406 into the aliquot chamber 408 where it can be isolated from the remaining portion of the sample within the collection chamber 406. The aliquot chamber 408 is in fluid communication with a dispensing tip 416 through a second one-way valve 412.

In one embodiment, illustrated in FIG. 4A, a plunger mechanism comprising a flexible squeeze bulb 414 defines the bottom perimeter of the aliquot chamber 408. The bulb 414 is constructed from a material that does not degrade in, or react with, water, alcohol, or PreservCyt®, and is biologically inert. Examples of such material include soft plastics, rubber, Tygon®, and the like.

An aliquot is collected when there is sample within the collection chamber 406, but not within the aliquot chamber 408. The user or an automated instrument (discussed below) depresses (pushes on) a flexible squeeze bulb 414. Air within the aliquot chamber 408 escapes through the valve 412. When the bulb 414 is released partial vacuum is created within the aliquot chamber 408, which causes fluid from the collection chamber 406 to flow through the valve 410 into the aliquot chamber 408. The bulb 414 is of such size that squeezing and releasing it once causes 4 mL of fluid to enter the aliquot chamber 408.

Once there is fluid within the aliquot chamber 408, the user can depress the bulb 414 to push the contents of the aliquot chamber 408 out through the valve 412 and the dispensing tip 416. The dispensed sample can be collected in a vial, as discussed below.

Preferably, a cap 418 covers the dispensing tip 416 when the tip 416 is not in use, i.e., when no solution is to be dispensed therethrough. The cap 418 is held in place covering the dispensing tip 416 by a friction lock or a nub and groove lock. Alternatively, the cap 418 is threaded on the dispensing tip 416. The cap 418 reduces the likelihood of outside contaminants contaminating the tip 416, and thereby contaminating any dispensed aliquots. Prior to dispensing the aliquot, the user removes the cap 418.

Figure 4B:
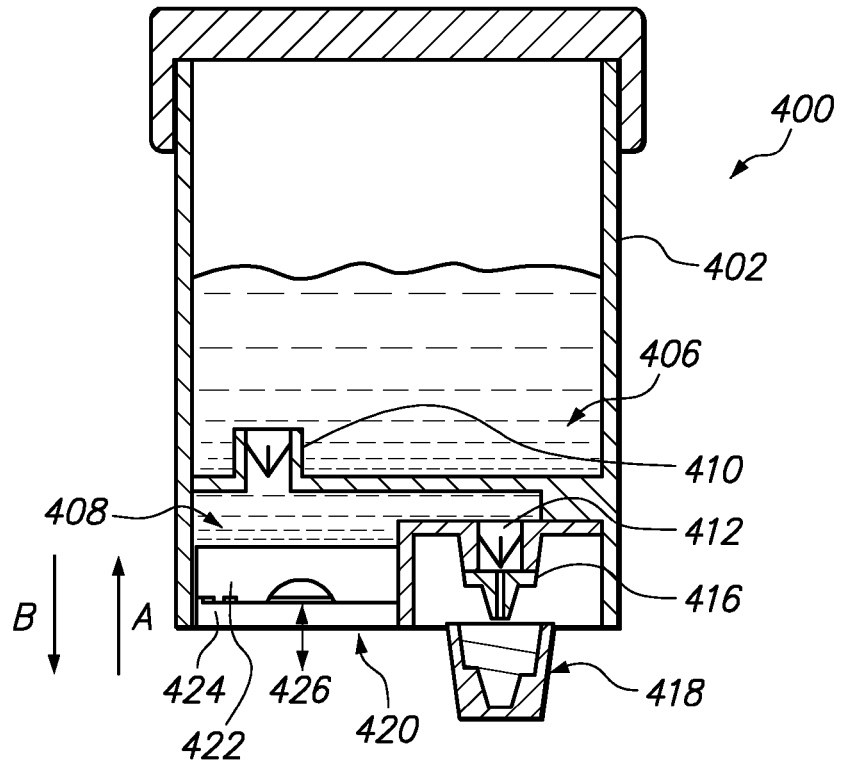
FIG. 4B is an illustration of another embodiment of a sample vial comprising an aliquot chamber at the bottom of the vial, where the aliquot chamber comprises a plunger mechanism.

In an alternative embodiment, illustrated in FIG. 4B, a plunger mechanism 420, comprising a piston 422 within a cylinder 424, is used to draw fluid into the aliquot chamber 408. The cylinder 424 is part of the body of the vial 400. A user or an automated instrument can move the piston 422 within the cylinder 424 in the direction of the arrows A and B by pushing in, or pulling out, the piston 422, respectively, using the handle 426. In some embodiments, the handle 426 may be specially configured for automated manipulation. For example, the handle 426 may have a bar across a crater where an automated arm can grasp the bar and move the piston 422. Alternatively, the handle 426 may be a knob or a boss that an automated arm can grasp.

Preferably, the cylinder 424 may have two blocking members (not shown) disposed about the periphery of the inside of the cylinder 424. One blocking member is at the top of the cylinder 424, while the other blocking member is at the bottom of the cylinder 424. The blocking members may be formed as rings or series of projections that extend radially inward from the inner walls of the cylinder 424. The blocking members may be used to arrest the movement of the piston 422 in the upward or downward direction, relative to the vial 400.

To prevent liquid escaping from the aliquot chamber 408, or contaminants entering the aliquot chamber 408, the piston 422 sealingly bears against the inner surface of the cylinder 424. To this end, the piston 422 has a diameter slightly smaller than the diameter of the cylinder 424 and an O-ring seal (not shown) seated within an annular recess (not shown) formed around the circumferential edge of the piston 422, so that the total diameter of the piston 422 is slightly greater than the diameter of the cylinder 424 in order to facilitate the sealing arrangement.

To collect an aliquot, the user or an automated instrument (discussed below) pushes the piston 422 in the direction of the arrow A, until the upper blocking member stops the piston 422 from traveling any further. Air within the aliquot chamber 408 escapes through the one-way valve 412. Alternatively, the vial 400 may be provided such that the piston 422 is located in its fully upward, relative to the vial 400, position. Piston 422 is then pulled in the direction of the arrow B until the lower blocking member stops the piston 422 from traveling any further. The downward, relative to the vial 400, movement of the piston 422 causes partial vacuum to be created within the aliquot chamber 408, which in turn causes fluid from the collection chamber 406 to flow through the one-way valve 410 into the aliquot chamber 408. The cylinder 424 is of such size that when piston 422 is pulled to its fully downward position 4 mL of fluid enters the aliquot chamber 408. Once there is fluid within the aliquot chamber 408, the user can push the piston 422 to its fully upward position to push the contents of the aliquot chamber 408 out through the valve 412 and the dispensing tip 416. The dispensed sample can be collected in a vial, as discussed below.

Figure 5:
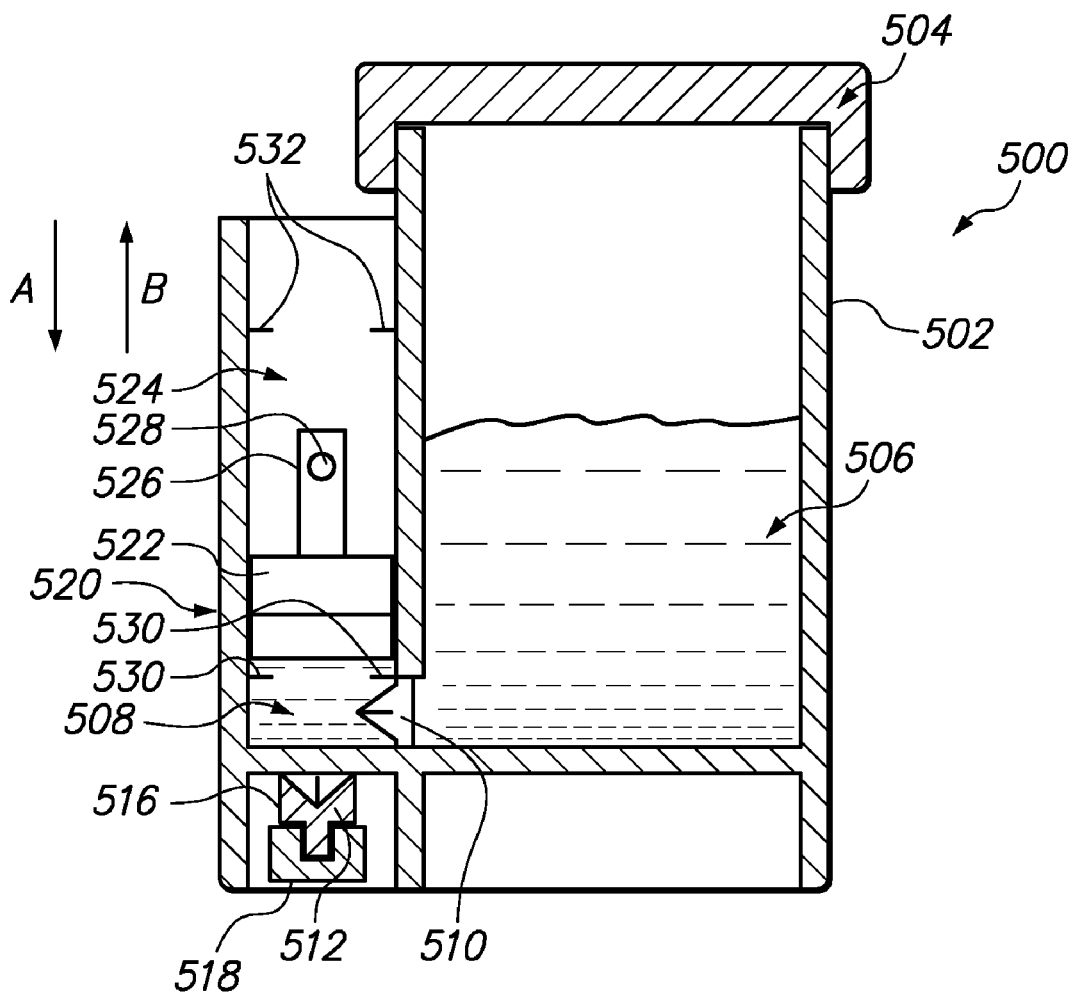
FIG. 5 is an illustration of another embodiment of a sample vial comprising an aliquot chamber at the side of the vial, where the aliquot chamber comprises a plunger mechanism.

Another embodiment of a vial having a second chamber is illustrated in FIG. 5. The vial 500 comprises a collection chamber 506 and an aliquot chamber 508. The aliquot chamber 508 is located to the side of the collection chamber 506. A lid 504 seals the top of the collection chamber 506.

A plunger mechanism 520, analogous to the plunger mechanism 420, discussed above, is used to draw fluid into the aliquot chamber 508. The plunger mechanism 520 comprises a piston 522 within a cylinder 524. The cylinder 524 is located to the side of the collection chamber 506 and shares a wall therewith. A user or an automated instrument can move the piston 522 within the cylinder 524 in the direction of the arrows A and B by pushing in, or pulling out, the piston 522, respectively, using the handle 526. In some embodiments, the handle 526 may be specially configured for automated manipulation. For example, in the embodiment shown, the handle 526 has a hole 528 into which a hook (not shown) of an automated arm can be inserted to move the piston 522. Alternatively, an automated arm can grasp the handle 526 and move the piston 522.

Preferably, the cylinder 524 may have two blocking members 530, 532 disposed about the periphery of the inside of the cylinder 524. One blocking member 532 is at the top of the cylinder 524, while the other blocking member 530 is at the bottom of the cylinder 524. The blocking members 530, 532 may be formed as rings or series of projections that extend radially inward from the inner walls of the cylinder 524. The blocking members may be used to arrest the movement of the piston 522 in the upward or downward direction, relative to the vial 500.

A sealing mechanism analogous to the one described for the piston 422 and cylinder 424 is also contemplated for the piston 522 in the cylinder 524 to prevent liquid escaping from the aliquot chamber 508, or contaminants entering the aliquot chamber 508.

To collect an aliquot, the user or an automated instrument (discussed below) pushes the piston 522 in the direction of the arrow A, until the lower blocking member 530 stops the piston 522 from traveling any further. Air within the aliquot chamber 508 escapes through the one-way valve 512. Alternatively, the vial 500 may be provided such that the piston 522 is located in its fully downward, relative to the vial 500, position. Piston 522 is then pulled in the direction of the arrow B until the upper blocking member 532 stops the piston 522 from traveling any further. The upward, relative to the vial 500, movement of the piston 522 causes partial vacuum to be created within the aliquot chamber 508, which in turn causes fluid from the collection chamber 506 to flow through the one-way valve 510 into the aliquot chamber 508. The cylinder 524 is of such size that when piston 522 is pulled to its fully upward position 4 mL of fluid enters the aliquot chamber 508.

In this embodiment, the aliquot chamber 508 is the same as the cylinder 524. The cylinder 524 refers to the space above the piston 522, into which fluid does not enter, and the aliquot chamber 508 refers to the space below the piston 522, which contains the aliquot.

Once there is fluid within the aliquot chamber 508, the user can push the piston 522 to its fully downward position to push the contents of the aliquot chamber 508 out through the valve 512 and the dispensing tip 516. The dispensed sample can be collected in a vial, as discussed below.

Preferably, a cap 518, analogous to the cap 418, covers the dispensing tip 416 when the tip 416 is not in use to prevent contamination. The cap 518 is held in place covering the dispensing tip 516 by a friction lock or a nub and groove lock, or alternatively, the cap 518 is threaded on the dispensing tip 516.

Figure 6:
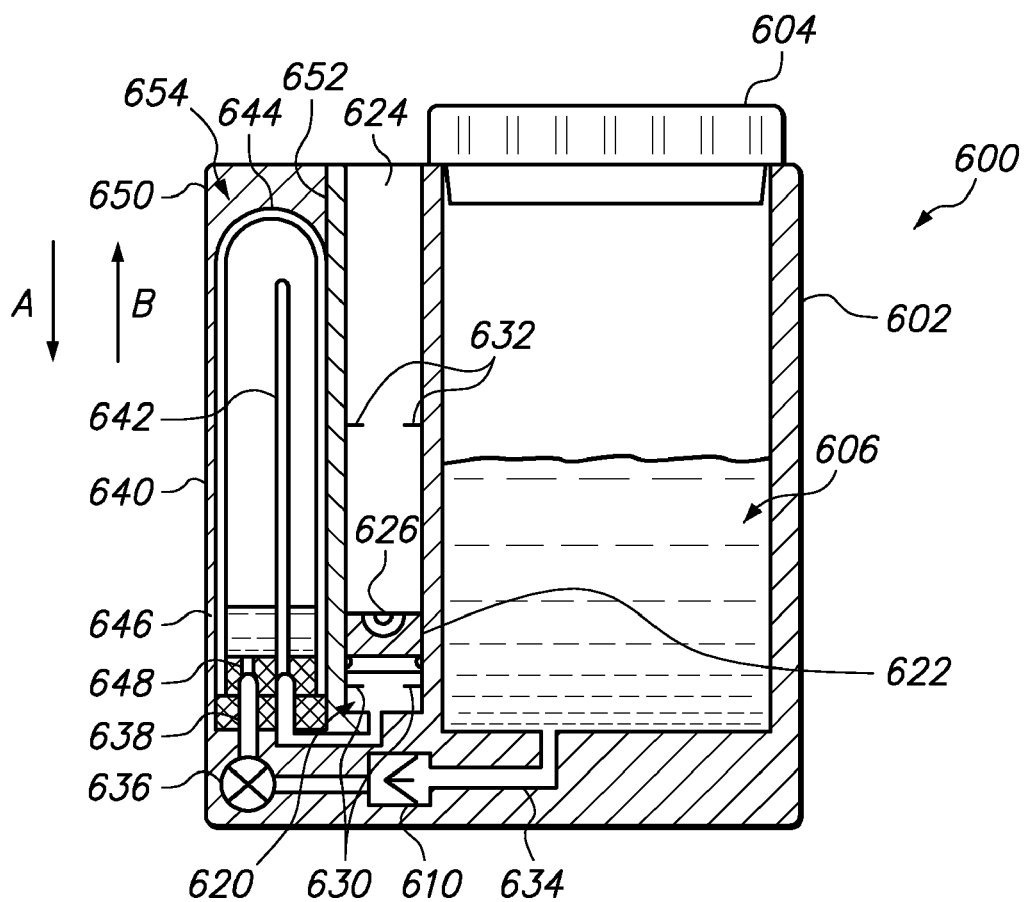
FIG. 6 is an illustration of another embodiment of a sample vial comprising a sample tube at the side of the vial.

Another embodiment of a sample vial is illustrated in FIG. 6. The vial 600 comprises a collection chamber 606. Adjoining the collection chamber 606 is a cylinder 624 housing a plunger mechanism 620. The plunger mechanism 620 comprises a piston 622, to which a handle 626 is connected. A sealing mechanism analogous to the one described for the piston 422 and cylinder 424 is also contemplated for the piston 622 in the cylinder 624. The sealing mechanism prevents air from the space above the piston 622 (hereinafter referred to as the top space of the cylinder 624) to enter the space below the piston 622 (hereinafter referred to as the bottom space of the cylinder 624), thereby ensuring a partial vacuum at the bottom space of the cylinder 624 when the piston 622 is pulled in the direction of the arrow B (see below). An air removal tube 642 is in gaseous communication with bottom space of the cylinder 624.

The collection chamber 606 is in fluid communication with a sample tube 640 through a passageway 634. A one-way valve 610 or a flow control valve 636 is along the passageway 634. The valve 610 allows fluid to flow from the collection chamber 606 towards the sample tube 640 but not in the reverse direction. When the flow control valve 636 is open fluid can flow along the passageway 634. Closing the flow control valve 636 prevents fluid from flowing along the passageway 634. In some embodiments only the flow control valve is along the passageway 634 and there is no one-way valve 610. In other embodiments, only the one-way valve 610 is along the passageway 634 and there is no flow control valve 634. Other embodiments, such as the one shown in FIG. 6, feature both the flow control valve 634 and the one-way valve 610.

The passageway 634 terminates at a blunt end 638 downstream from the flow control valve 634. As shown in FIG. 6, the blunt end 638 of the passageway 634 points upward relative to the vial 600.

A removable sample tube 640 is provided comprising a closed end 644 and an open end 646. The open end 646 is capped with a self-sealing cap 648, for example a septum. When the sample tube 640 is connected to the vial 600, it is inverted such that the capped open end 646 is facing downward, proximal to the flow control valve 634, and the closed end 644 is facing upward, proximal to the vial cap 604. Preferably, walls 650 and 652 create a chamber 654 into which the sample tube 640 is inserted. To connect the sample tube 640, it is inverted and placed in the chamber 654. The tube 640 is then pushed down until the air tube 642 and the blunt end 638 penetrate the self-sealing cap 648. The self-sealing cap 648 creates an air- and fluid-tight seal around the passageway 634 and the air tube 642. Before inserting a sample tube 640 to collect an aliquot, the user pushes down on the piston 622 in the direction of the arrow A until the lower blocking member 630 stops the piston 622 from traveling any further.

To collect an aliquot, the user inserts the sample tube 640 and opens the flow control valve 636. Next, the user pulls on the piston 622 in the direction of the arrow B, until the upper blocking member 632 stops the piston 622 from traveling any further. The upward, relative to the vial 600, movement of the piston 622 causes air to flow out of the sample tube 640, through the air tube 642 and into the bottom end of the cylinder 624, thereby creating a partial vacuum in the sample tube 640. The partial vacuum in the sample tube 640 in turn causes fluid from the collection chamber 606 to flow through the passageway 634, the one-way valve 510, the flow control valve 636, and the blunt end 638 and into the sample tube 640. The cylinder 624 is of such size that when piston 622 is pulled to its fully upward position 4 mL of fluid enters the sample tube 640. Prior to removing the sample tube 640, the user closes the flow control valve 636. The sample tube 640 can be removed at any time according to the discretion of the user.

Figure 7:
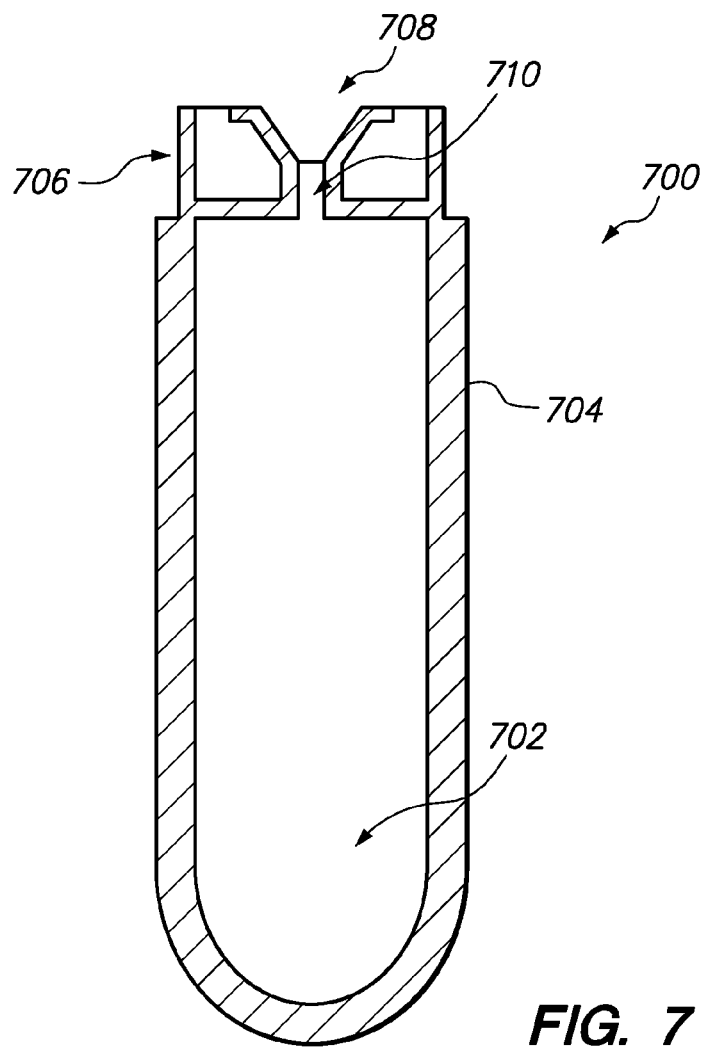
FIG. 7 is an illustration of an embodiment of a sample tube.

When an aliquot of the sample is removed from a vial 400 or 500 for further examination, the aliquot is dispensed in a sample tube. FIG. 7A illustrates an embodiment of the sample tube 700. The sample tube 700 comprises a sample chamber 702 defined by the body 704 of the tube. The body 704 is similar to a common test tube or a BD Falcon™ centrifuge tube. The body 704 can be constructed from glass, plastics, and the like. The volume of the sample chamber 702 is usually greater than 4 mL so that a 4 mL aliquot of the sample can conveniently fit in the chamber 702.

The sample tube 700 further comprises a receiving head 706. The receiving head 706 can be molded on the body 704 during manufacturing. Alternatively, the receiving head 706 is put on the body 704 subsequent to the manufacturing. The receiving head 706 can be threaded on the upper part of the body 704 or it can fit on, and stay on, the body 704 by friction.

The receiving head 706 comprises a flared receiving funnel 708, which is in fluid communication with the sample chamber 702 through a passageway 710. The funnel 708 is adapted to sealably mate with the dispensing tips 416 and 516. In some embodiments, the receiving head 706 threadably connects with the dispensing tip 416, 516. Alternatively, the receiving head 706 connects with the dispensing tip 416, 516 by a friction lock mechanism. Often, the same mechanism that is used to cap the dispensing tip 416, 516 with a cap 418, 518 is also used to connect the receiving head 706 with the dispensing tip 416, 516.

To dispense an aliquot from the vial 400, 500 into a sample tube 700, an aliquot of the sample is drawn from the collection chamber 406, 506 into the aliquot chamber 408, 508, as discussed above. The dispensing tip 416, 516 is uncapped and the sample tube 700 is connected to the vial, such that the receiving head 706 mates with the dispensing tip 416, 516, as discussed above. The aliquot is caused to be dispensed into the sample tube 700 by either pushing on the flexible squeeze bulb 414, pushing the piston 422 upward, or pushing the piston 522 downward, depending on the particular embodiment of vial used.

Having described the structure and function of several embodiments of sample vials, a method of processing a sample vial will now be described in the context of triaging patients for precursors of cervical cancer.

First, the vial cap is removed from the vial container and a fluid-based cervical-vaginal sample is placed within the collection chamber of the vial container. This step can typically be accomplished at the physician's office, as part of the routine Pap smear. In particular, cells are scraped from the cervix of the patient and mixed into a preservative solution, such as PreservCyt® transport medium, contained within the collection chamber of the vial container. Next, the vial cap is placed back on the vial container, the vial is labeled with pertinent information, such as the patient's name, medical records number, physician's name, etc., and the vial with the collected fluid-based sample, is transferred to a cytological laboratory.

At the cytological laboratory, the fluid-based sample is agitated to disburse the cells, and an aliquot of the sample is obtained while the vial cap is mated with the vial container, as described above for the various embodiments of the vial.

In the embodiments illustrated in FIGS. 1, 2B, and 2C, this is accomplished by unscrewing the cap 114, inserting a syringe or a pipette into the vial container 102, and drawing about 4 mL of the sample into the syringe or the pipette. The syringe or the pipette is then removed and the cap 114 is screwed back on the vial cap 104. The aliquot is then placed inside a sample tube 704 or another container. In the embodiments illustrated in FIGS. 1, 2D and 3A, this is accomplished by inserting a syringe into the vial container 102 through the septum 116 and drawing about 4 mL of the sample into the syringe or the pipette. The syringe is then removed and the aliquot is then placed inside the sample chamber 702 of a sample tube 700 or another container.

In the embodiments illustrated in FIGS. 4A, 4B, 5, and 6, the aliquot is removed from the collection chamber 406, 506, 606 and is placed in the aliquot chamber 408, 508, 608 as discussed above. Upon the discretion of the user, the removed aliquot can remain in the aliquot chamber throughout the remainder of the procedure, or the removed aliquot can be dispensed into a sample tube 704 or another container.

In some embodiments, the volume of the sample in the collection chamber is replenished by adding more solvent, equivalent in volume to the volume of the removed aliquot, to the collection chamber. For example, 4 mL of PreservCyt® is added to the sample in the collection chamber to bring the volume of the sample in the vial back up to the original 20 mL.

Next, the vial cap is unmated from the vial container to expose, and thereby provide access, to the remaining sample portion in the collection chamber, and at least some of the remaining sample portion is transferred from the collection chamber to a microscope slide while the aliquot chamber is sealed from the collection chamber (embodiments of FIGS. 4A, 4B, 5, and 6). Typically, exposing the collection chamber to the external environment may expose the remaining sample portion to contaminants (e.g., HPV) at the molecular level. This may be especially true if the slide preparation process is performed by an automated specimen preparation system where molecular contaminants are often found. Without taking additional precautions, such molecular contaminants can be found in an aerosol or within filtered cell solution in the plumbing of the automated specimen preparation system where it can be transferred from vial to vial. However, because the aliquot sample in the aliquot chamber is isolated from the collection chamber, it will not be exposed to any contaminants that may enter the collection chamber.

Next, the slide specimen is reserved for cytological screening of the sample for precursors of cervical cancers, and the sample aliquot is reserved for DNA testing, e.g., for the present of high-risk HPV in the sample. Next, the slide is cytological screened, e.g., for precursors of cervical cancers. This can be accomplished in the same laboratory at which the slide was prepared, or alternatively, can be transferred to another laboratory. In the case where no abnormal cells are found, the patient is returned to a routine Pap smear schedule. In the case of an ASC-US+ result, the patient is scheduled for a colposcopy/biopsy at the physician's office. In the case of an ASC-US result, the aliquot sample is removed from the aliquot chamber via the dispensing tip 416, 516 (embodiments of FIGS. 4A, 4B, and 5) or the sample tube 640 is removed from the chamber 654 (embodiment of FIG. 6), and a reflex DNA test is performed on the aliquot sample for the presence of high-risk HPV. This can be accomplished using Digene's Hybrid Capture II HPV DNA assay. If the presence of high-risk HPV is detected in the sample, the patient is scheduled for a colposcopy/biopsy at the physician's office, or alternatively may be placed on a schedule with increased Pap smear intervals. If the presence of high-risk HPV is not detected in the sample, the patient may then be returned to a routine Pap smear schedule. Optionally, other DNA tests, e.g., to detect the presence of such as *Chlamydia trachomatis* and *Neisseria gonorrhoeae*, may be performed. These other DNA tests, or even the HPV DNA test, can be alternatively performed in parallel with the cytological screening of the slide.

The use of vial 400, 500, and 600 allows the user to obtain and store an aliquot prior to the preparation of a slide sample by, for example, ThinPrep® 2000 or ThinPrep® 3000. This imparts the advantage significantly minimizing the likelihood of contamination of the aliquot due to the ThinPrep process.

In some embodiments, an instrument is provided for automatically transferring an aliquot of a biological sample from the collection chamber of a vial to a sample tube. In one such embodiment, a vial is placed within the instrument. In certain embodiments, individual vials are placed within the instrument. In other embodiments, the vials are placed on or within an input tray and the input tray is placed within the instrument. By "within the instrument" it is meant that the vial is placed within the reach of a first mechanical arm used for retrieving the vials. Thus, in some embodiments, the vial or the tray is placed in close proximity to the instrument, whereas in other embodiments, the first mechanical arm is within an enclosed chamber and the vial or the input tray is placed inside the enclosed chamber. In some embodiments, the instrument further comprises a transport mechanism, upon which the vial or the input tray is placed and is then transported to an area of the instrument within the reach of the first mechanical arm.

In some embodiments, the first mechanical arm grabs the vial by its cap, whereas in other embodiments, the first mechanical arm grabs the vial by its body. In other embodiments, the first mechanical arm lifts the vial from the bottom of the vial.

In certain embodiments, the instrument further comprises an agitator. The agitator mixes the contents of the vial to break up blood, mucous and/or cell clusters and to disburse the cells within the sample. In some embodiments, the agitator rotates the vial at relatively high rotational speeds. In other embodiments, the agitator shakes the vial. In still other embodiments, the agitator is a sonicator that applies ultrasound energy to agitate the contents of the vial.

In some embodiments, the first mechanical arm picks up the vial and deposits it at the agitator. In certain embodiments, the first mechanical arm continues to hold onto the vial while the contents of the vial are agitated. In other embodiments, the first mechanical arm releases the vial at the agitator. In the embodiments that an agitator is used, following the agitation step an aliquot is obtained. In the embodiments where an agitator is not used, an aliquot is obtained after the first mechanical arm picks up the vial.

For obtaining an aliquot from the vials illustrated in FIGS. 1, 2B, and 2C, the instrument comprises an actuator that rotates the cap 114 in a counter-clockwise direction to unscrew the cap. The actuator then lifts the cap away from the port 110. In these embodiments, the instrument further comprises a syringe in gaseous communication with a vacuum source. The syringe is inserted into the vial container 102 through the port 110 and a volume, such as 4 mL, of liquid is removed by vacuum suction from the vial container 102. The syringe is then removed from the vial and then directed to a sample tube. The removed aliquot is then dispensed into the sample tube. The actuator that was used to remove the cap 114 then replaces the cap 114 and rotates it in a clockwise direction to tighten the cap. In the embodiments illustrated in FIGS. 1, 2D and 3A, the syringe is directly inserted into the port 110 through the septum 116 and the aliquot is removed. After dispensing the aliquot in the sample tube, the vial and the sample tube are delivered to an output tray, as discussed below.

In some embodiments, the syringe is disposable, i.e., each syringe is used only once to remove a sample from a vial. The use of disposable syringes minimizes the chance of cross-contamination between the vials. Each syringe comprises a needle and a body, where the body is capable of holding at least 4 mL of fluid. In these embodiments, a hose connects the vacuum source to a head. The head is configured to removably attach the syringe. The syringe is attached to the head, and after the needle of the syringe is inserted into the vial container, a volume, e.g., 4 mL, of solution is removed. After the aliquot is dispensed in a sample tube, the syringe is detached from the head, whereupon the head obtains another syringe to obtain an aliquot of solution from the next vial.

For obtaining an aliquot from the vial illustrated in FIG. 4A, the instrument comprises a first actuator adapted to press on the flexible squeeze bulb 414 and release it, thereby filling the aliquot chamber 408. In some embodiments, the instrument returns the vial to an output tray (see below) after the aliquot chamber 408 is filled. In other embodiments, it is desirable to remove the aliquot from the aliquot chamber 408 and dispense it into a sample tube 700. In these embodiments, a second mechanical arm obtains a sample tube 700 either from the input tray or from a sample tube repository within the instrument (see below). If the sample tube 700 is capped, a second actuator uncaps the sample tube 700. An actuator, either the second actuator or a different one, removes the cap 418 of the vial 400. The second mechanical then connects the receiving head 706 of the sample tube 700 to the dispensing tip 416 of the vial 400. The first actuator then presses on the flexible squeeze bulb 414 to dispense the aliquot from the aliquot chamber 408 into the sample chamber 702 of the sample tube 700. The second mechanical arm then removes the sample tube 700 from the dispensing tip 416. The second actuator caps the sample tube 700 and places the sample tube 700 into an output tray. The first mechanical arm then places the vial 400 into an output tray.

For obtaining an aliquot from the vials illustrated in FIGS. 4B, 5, and 6, the instrument comprises a first mechanical arm that retrieves the vial from an input tray, and optionally transports it to an agitator. The instrument further comprises a second mechanical arm terminating in a grasper. Following the optional agitation, the second mechanical arm is brought to the proximity of the handle 426, 526, and 626, respectively. The grasper is adapted to grasp the handle 426, 526, and 626, respectively, while the second mechanical arm moves the piston 422, 522, and 622, respectively, in the direction of the arrows A and B. The second mechanical arm first moves the piston 422, 522, and 622, respectively, in the direction of the arrow A until blocking members stop the piston 422, 522, and 622, respectively, from traveling any further. At this stage, in the embodiment of FIG. 6, a first actuator opens the flow control valve 636. The second mechanical arm then moves the piston 422, 522, and 622, respectively, in the direction of the arrow B until the blocking members stop the piston 422, 522, and 622, respectively, from traveling any further. At this stage, an aliquot is obtained in the aliquot chamber 408, 508, and sample tube 640, respectively. In the embodiment of FIG. 6, the first actuator closes the flow control valve 636.

In some embodiments, the instrument returns the vial 400, 500 to an output tray (see below) after an aliquot is obtained in the aliquot chamber 408, and 508, respectively. In other embodiments, it is desirable to remove the aliquot from the aliquot chamber 408, and 508, respectively, and dispense it into a sample tube 700. In these embodiments, a third mechanical arm obtains a sample tube 700 either from the input tray or from a sample tube repository within the instrument (see below). If the sample tube 700 is capped, a second actuator uncaps the sample tube 700. An actuator, either the second actuator or a different one, removes the cap 418 or 518, respectively, of the vial 400, 500, respectively. The third mechanical arm then connects the receiving head 706 of the sample tube 700 to the dispensing tip 416, 516, respectively, of the vial 400, 500, respectively. The second mechanical arm then moves the piston 422, 522, respectively, in the direction of the arrow A until the blocking members stop the piston 422, 522, respectively, from traveling any further. Consequently, the aliquot is dispensed from the aliquot chamber 408, and 508, respectively into the sample chamber 702 of the sample tube 700. The third mechanical arm then removes the sample tube 700 from the dispensing tip 416, 516, respectively. The second actuator caps the sample tube 700 and places the sample tube 700 into an output tray. The first mechanical arm then places the vial 400, 500, respectively into an output tray.

In some embodiments, the aliquot chamber 408, 508, or sample tube 640 is surrounded by opaque walls. In these embodiments, it is difficult to visually ascertain whether a certain vial has been through the instrument and its aliquot chamber is filled or not. Thus, in some embodiments, the instrument further comprises a marker. Once the aliquot chamber 408, 508, or sample tube 640 is filled, the marker marks the vial in a specified location. The marking on the vials allows a user to quickly determine whether the aliquot chamber of the particular vial has been filled.

As discussed above, the minimum amount of sample in the vial container 102, 402, 502, 602 required by the Food and Drug Administration (FDA) for automated transfer onto a microscope slide using Cytyc's ThinPrep® 2000 or Thinprep® 3000 slide preparation systems is 20 mL. Thus, in some embodiments, the instrument further comprises a re-fill mechanism. The re-fill mechanism comprises a storage tank for holding a liquid into which the biological sample is suspended. Examples of such liquid include, but are not limited to, water, saline, a buffer solution, such as phosphate buffer saline (PBS), 4-(2-hydroxyethyl)-1-piperazineethanesulfonic acid solution, (HEPES), and the like, or a commercially available solution, such as PreservCyt® (Cytyc Corp., MA). In some embodiments, the re-fill mechanism re-fills the vial after the aliquot chamber 408, 508, or sample tube 640 has been filled with the same solution that was used to dissolve the biological sample, and for the same volume as that of the aliquot chamber 408, 508, or sample tube 640. In some embodiments, the vial container 102, 402, 502, 602 holds 20 mL, and the aliquot chamber 408, 508, or sample tube 640 holds 4 mL. When the aliquot chamber is filled, the volume of fluid in the vial container 102, 402, 502, 602 is reduced to 16 mL. In these embodiments, the re-fill mechanism adds another 4 mL to the vial container 102, 402, 502, 602.

In the embodiment of FIGS. 3A, 3B, instead of a re-fill mechanism, the instrument comprises an actuator that presses on the flexible membrane 314 in order to release the solution 306 in the solution chamber 302.

Figure 8:
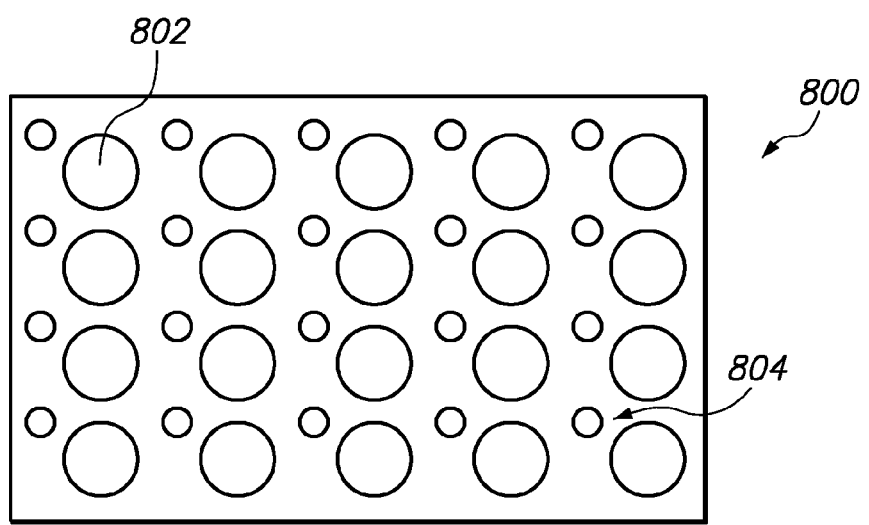
FIG. 8 is an illustration of an embodiment of a sample tray with slots for both vials and sample tubes.

In some embodiments, the input tray comprises a plurality of slots for the vials, into each one of which an individual vial is placed prior to placing the input tray within the instrument. In alternative embodiments, such as the one illustrated in FIG. 8, the input tray 800 comprises a plurality of slots 802 for the vials 100, 300, 400, 500 (vial slots), in addition to a plurality of slots 804 for sample tubes 700 (tube slots). Preferably, there are as many vial slots 802 as there are tube slots 804. More preferably, there is a unique, one-to-one relationship between each vial slot 802 and tube slot 804, such that a tube slot 804 is located adjacent to its corresponding vial slot 802, and the tube 700 located in a tube slot 804 will contain an aliquot of the sample obtained from a vial 100, 300, 400, 500 located in the adjacent vial slot 802.

Figure 9:
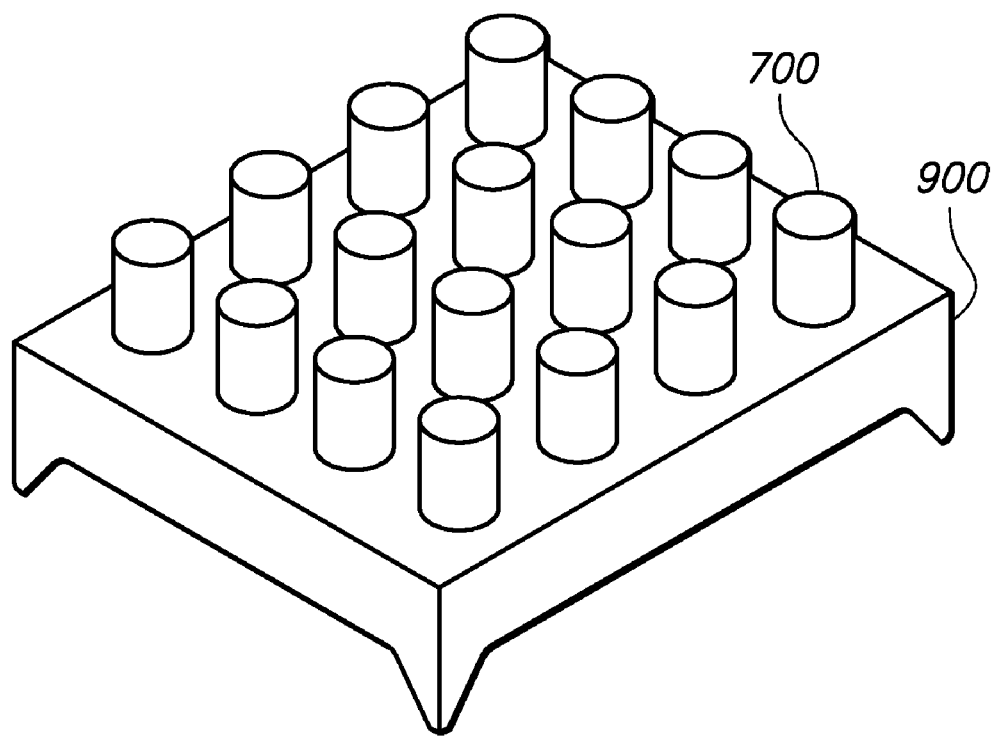
FIG. 9 is an illustration of another embodiment of a sample tray with slots for sample tubes.

In the embodiments where the input tray comprises only vial slots and not tube slots, the instrument comprises a location for holding a plurality of sample tubes 700. When the user chooses a removed aliquot to be dispensed into a sample tube, the instrument obtains a sample tube 700 and dispenses the aliquot into it. The instrument then labels the sample tube 700 with the same identifying marks as appear on the vial label, e.g., the name of the patient, the medical record number, etc. The instrument then places the vials and the sample tubes into an output tray. In these embodiments, the output tray is the tray 800, shown in FIG. 8. Alternatively, two separate output trays are used. One output tray is used for vials, and one output tray is used for sample tubes. FIG. 9 shows an embodiment of an output tray 900 used for vials 700.

In some embodiments, tray 800 is used as both the output tray and the input tray. The vials and the sample tubes are arranged on a tray and are then put within the instrument. A first mechanical arm removes a vial from the tray and a second mechanical arm removes a sample tube from the tray. After the instrument has completed the task of obtaining an aliquot and dispensing the aliquot in the sample tube, the first mechanical arm returns the vial to the same location from whence it was removed and the second mechanical arm returns the sample tube to the same location from whence it was removed.

In other embodiments, the input tray and the output tray are different. In still other embodiments, the instrument disclosed herein is coupled with an automated slide processor, such as ThinPrep® 2000 or Thinprep® 3000 slide preparation systems (Cytyc Corp., MA). In these embodiments, once the aliquot chamber is filled or an aliquot is dispensed in a sample tube, the mechanical arm places the vial in a location where the vial can be used in the automated slide processor.

Although particular embodiments of the present invention have been shown and described, it should be understood that the above discussion is not intended to limit the present invention to these embodiments, and it will be readily apparent to those skilled in the art that various changes and modifications may be made without departing from the invention, as defined by the claims.

The invention claimed is:

1. A biological sample container, comprising a vial configured for holding a liquid-based biological sample;
    a vial cap configured to removably seal the vial; and
    an access port comprising an opening through the vial cap and a self-sealing septum disposed within the opening, wherein the access port is adapted to admit a needle therethrough for obtaining an aliquot of the biological sample from the vial; and
    a solution chamber within the vial cap, wherein the access port is located adjacent to the solution chamber such that the access port provides needle access to the vial but not to the solution chamber, the chamber comprising a sealable opening, the chamber further comprising a flexible membrane incorporated into the vial cap, the flexible membrane configured to open the sealable opening when the flexible membrane is depressed,
    wherein the sealable opening is sealed by an openable flap held in a closed position by a locking mechanism that is released by depressing the flexible membrane.

2. The container of claim 1, wherein the septum is a rubber septum.

3. The container of claim 1, wherein the sealable opening faces an interior of the vial.

4. The container of claim 3, wherein the flexible membrane coplanar with a top surface of the vial cap.

5. A method of obtaining an aliquot of a liquid-based biological sample disposed in a container, wherein the container is a biological sample container, comprising
    a vial configured for holding a liquid-based biological sample;
    a vial cap configured to removably seal the vial; an access port comprising an opening through the vial care and a self-sealing septum disposed within the opening, wherein the access port is adapted to admit a needle therethrough for obtaining an alquot of the biological sample from the vial; and
    a solution chamber within the vial cap, wherein the access port is located adjacent to the solution chamber such that the access port provides needle access to the vial but not to the solution chamber, the chamber comprising a sealable opening, the chamber further comprising a flexible membrane incorporated into the vial care, the flexible membrane configured to open the sealable opening when the flexible membrane is depressed,
    wherein the sealable opening is sealed by an openable flap held in a closed position by a locking mechanism that is released by depressing the flexible membrane, the method comprising:
    placing the container inside an automated processor;
    automatically inserting a syringe through the septum and into the vial; drawing an aliquot of the biological sample into the syringe; automatically removing the syringe from the vial by withdrawing the syringe back through the septum;
    dispensing the transferred aliquot of the biological sample from the syringe into a sample tube; and placing the container and the sample tube in an output tray.

6. The method of claim 5, wherein the aliquot of the biological sample is drawn into the syringe using vacuum.

7. The method of claim 5, further comprising capping the sample tube after dispensing the transferred aliquot.

8. The method of claim 5, further comprising placing the container in a first output tray and placing the sample tube in a second output tray.

9. The container of claim 1, wherein the solution chamber is configured to hold a volume of solution that is substantially equal to a volume of the aliquot of the biological sample.

10. The container of claim 3, wherein the sealable opening is sealed by a flap is configured to pivot about a hinge.

11. The method of claim 4, wherein the sealable opening faces an interior of the vial and the flexible membrane is coplanar with a top surface of the vial cap, the method further comprising adding a volume of solution to the vial by depressing the flexible membrane, thereby opening the sealable opening in the solution chamber so that the volume of solution flows from the solution chamber into the vial.

* * * * *